US011744692B2

(12) United States Patent
Farago et al.

(10) Patent No.: US 11,744,692 B2
(45) Date of Patent: Sep. 5, 2023

(54) MEDICAL DRAIN DEVICE

(71) Applicant: BOSTON SCIENTIFIC SCIMED, INC., Maple Grove, MN (US)

(72) Inventors: Laszlo Trent Farago, Hudson, WI (US); Mark A. Hilse, Ham Lake, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1472 days.

(21) Appl. No.: 15/903,883

(22) Filed: Feb. 23, 2018

(65) Prior Publication Data
US 2018/0235743 A1 Aug. 23, 2018

Related U.S. Application Data

(60) Provisional application No. 62/462,692, filed on Feb. 23, 2017.

(51) Int. Cl.
*A61F 2/01* (2006.01)
*A61M 39/22* (2006.01)
(Continued)

(52) U.S. Cl.
CPC .......... *A61F 2/013* (2013.01); *A61B 17/1204* (2013.01); *A61B 17/12109* (2013.01);
(Continued)

(58) Field of Classification Search
CPC .......... A61F 2/013; A61F 2/966; A61F 2/962; A61F 2230/0067; A61B 17/1204;
(Continued)

(56) References Cited

U.S. PATENT DOCUMENTS 4,080,965 A * 3/1978 Phillips ................ A61M 39/14
604/905
4,249,946 A 2/1981 Danielson
(Continued)

FOREIGN PATENT DOCUMENTS

EP 0775470 A1 5/1997
FR 2939637 A1 6/2010
(Continued)

OTHER PUBLICATIONS

International Search Report and Written Opinion dated May 9, 2018 for International Application No. PCT/US2018/019511.
(Continued)

*Primary Examiner* — Nathan R Price
*Assistant Examiner* — Mark A Igel
(74) *Attorney, Agent, or Firm* — Seager, Tufte & Wickhem LLP

(57) ABSTRACT

A medical device may include an elongate tubular member defining a tube lumen, and an expandable member disposed on the distal portion of the elongate tubular member including a lumen that is in fluid communication with the tube lumen. The expandable member is configured to expand from a collapsed delivery configuration to a distally-open expanded configuration and establish apposition with a vessel wall. A valve member in fluid communication with the tube lumen, and configured to selectively block and selectively allow for flow through the tube lumen. The device may be percutaneously-deployable downstream of a treatment site within a body lumen and may allow for selective removal and/or draining of fluid and/or material, such as embolic material, from a body lumen.

17 Claims, 10 Drawing Sheets

(51) Int. Cl.
*A61B 17/12* (2006.01)
*A61B 17/3207* (2006.01)
*A61B 17/221* (2006.01)
*A61M 25/10* (2013.01)
*A61B 17/22* (2006.01)
*A61B 90/00* (2016.01)
*A61B 17/00* (2006.01)

(52) U.S. Cl.
CPC .......... *A61B 17/22* (2013.01); *A61M 25/104* (2013.01); *A61M 39/22* (2013.01); *A61B 2017/00893* (2013.01); *A61B 2017/2215* (2013.01); *A61B 2017/22079* (2013.01); *A61B 2017/22084* (2013.01); *A61B 2017/320716* (2013.01); *A61B 2090/3966* (2016.02); *A61B 2217/007* (2013.01); *A61F 2230/0067* (2013.01)

(58) Field of Classification Search
CPC .............. A61B 17/12109; A61B 17/22; A61B 2090/3966; A61B 2017/00893; A61B 2017/22079; A61B 2017/22084; A61B 2017/2215; A61B 2017/320716; A61B 2017/007; A61M 25/104; A61M 39/22
See application file for complete search history.

(56) References Cited

U.S. PATENT DOCUMENTS

| | | | |
|---|---|---|---|
| 4,873,978 A * | 10/1989 | Ginsburg | 606/198 |
| 4,896,669 A * | 1/1990 | Bhate | A61M 25/1006 604/917 |
| 4,921,479 A | 5/1990 | Grayzel | |
| 4,990,151 A | 2/1991 | Wallstén | |
| 4,994,072 A * | 2/1991 | Bhate | A61M 25/1038 604/917 |
| 5,026,377 A * | 6/1991 | Burton | A61F 2/95 606/108 |
| 5,049,131 A * | 9/1991 | Deuss | A61M 25/1002 606/194 |
| 5,160,321 A * | 11/1992 | Sahota | A61M 25/1002 604/101.02 |
| 5,196,024 A * | 3/1993 | Barath | A61B 17/320725 606/191 |
| 5,226,887 A * | 7/1993 | Farr | A61M 25/1027 604/103.09 |
| 5,295,995 A * | 3/1994 | Kleiman | A61M 25/104 604/103.07 |
| 5,308,356 A * | 5/1994 | Blackshear, Jr. | A61M 25/1002 606/194 |
| 5,318,587 A * | 6/1994 | Davey | A61M 25/1038 604/103.14 |
| 5,320,634 A * | 6/1994 | Vigil | A61B 17/320725 604/103.08 |
| 5,336,234 A * | 8/1994 | Vigil | A61M 25/104 606/171 |
| 5,366,504 A | 11/1994 | Andersen et al. | |
| 5,411,552 A | 5/1995 | Andersen et al. | |
| 5,458,572 A * | 10/1995 | Campbell | A61M 25/104 604/103.08 |
| 5,490,839 A * | 2/1996 | Wang | A61M 25/1038 604/103 |
| 5,545,132 A * | 8/1996 | Fagan | A61M 25/1002 604/103.08 |
| 5,645,529 A * | 7/1997 | Fagan | A61M 25/1011 604/101.01 |
| 5,649,941 A * | 7/1997 | Lary | A61B 17/3207 606/171 |
| 5,662,671 A * | 9/1997 | Barbut | A61B 17/3207 606/159 |
| 5,693,014 A * | 12/1997 | Abele | A61M 25/1002 604/103.08 |
| 5,704,913 A * | 1/1998 | Abele | A61M 25/104 604/101.02 |
| 5,709,703 A | 1/1998 | Lukic et al. | |
| 5,746,745 A * | 5/1998 | Abele | A61M 25/1002 604/103.08 |
| 5,772,609 A | 6/1998 | Nguyen et al. | |
| 5,772,669 A | 6/1998 | Vrba | |
| 5,827,227 A | 10/1998 | DeLago | |
| 5,868,708 A * | 2/1999 | Hart | A61M 25/1002 604/107 |
| 5,893,868 A * | 4/1999 | Hanson | A61F 2/0095 606/198 |
| 5,947,925 A * | 9/1999 | Ashiya | A61M 25/0169 604/164.08 |
| 5,971,938 A * | 10/1999 | Hart | A61B 17/22031 606/127 |
| 5,997,508 A | 12/1999 | Lunn et al. | |
| 6,090,072 A | 7/2000 | Kratoska et al. | |
| 6,139,510 A | 10/2000 | Palermo | |
| 6,183,443 B1 | 2/2001 | Kratoska et al. | |
| 6,210,370 B1 * | 4/2001 | Chi-Sing | A61B 17/22032 604/104 |
| 6,264,671 B1 | 7/2001 | Stack et al. | |
| 6,361,545 B1 * | 3/2002 | Macoviak | A61B 17/221 606/151 |
| 6,395,014 B1 | 5/2002 | Macoviak et al. | |
| 6,431,271 B1 | 8/2002 | Thomeer et al. | |
| 6,433,979 B1 | 8/2002 | Yu et al. | |
| 6,488,702 B1 | 12/2002 | Besselink | |
| 6,582,460 B1 | 6/2003 | Cryer | |
| 6,592,549 B2 | 7/2003 | Gerdts et al. | |
| 6,607,551 B1 | 8/2003 | Sullivan et al. | |
| 6,645,239 B1 | 11/2003 | Park et al. | |
| 6,669,680 B1 | 12/2003 | Macoviak et al. | |
| 6,695,864 B2 | 2/2004 | Macoviak et al. | |
| 6,884,259 B2 | 4/2005 | Tran et al. | |
| 6,902,575 B2 * | 6/2005 | Laakso | A61F 2/95 623/1.11 |
| 6,960,215 B2 * | 11/2005 | Olson, Jr. | A61B 17/7097 606/53 |
| 6,997,939 B2 | 2/2006 | Linder et al. | |
| 7,083,633 B2 | 8/2006 | Morrill et al. | |
| 7,127,789 B2 | 10/2006 | Stinson | |
| 7,137,991 B2 | 11/2006 | Fedie | |
| 7,252,650 B1 * | 8/2007 | Andrews | A61F 2/958 604/103.09 |
| 7,300,456 B2 | 11/2007 | Andreas et al. | |
| 7,468,070 B2 | 12/2008 | Henry et al. | |
| 7,473,271 B2 | 1/2009 | Gunderson | |
| 7,585,309 B2 * | 9/2009 | Larson | A61F 2/0105 606/200 |
| 7,591,832 B2 | 9/2009 | Eversull et al. | |
| 7,604,650 B2 | 10/2009 | Bergheim et al. | |
| 7,762,995 B2 | 7/2010 | Eversull et al. | |
| 7,875,051 B2 | 1/2011 | Beulke et al. | |
| 7,887,574 B2 | 2/2011 | McFerran | |
| 7,935,075 B2 * | 5/2011 | Tockman | A61N 1/057 604/101.02 |
| 8,114,114 B2 | 2/2012 | Belson | |
| 8,206,412 B2 | 6/2012 | Galdonik et al. | |
| 8,252,016 B2 | 8/2012 | Anwar | |
| 8,287,564 B2 | 10/2012 | Beulke et al. | |
| 8,308,754 B2 | 11/2012 | Belson | |
| 8,444,685 B2 | 5/2013 | Gerdts et al. | |
| 8,535,368 B2 | 9/2013 | Headley, Jr. et al. | |
| 8,668,728 B2 | 3/2014 | Headley et al. | |
| 8,696,698 B2 * | 4/2014 | Chomas | A61F 2/014 606/200 |
| 8,764,816 B2 | 7/2014 | Koss et al. | |
| 8,834,550 B2 | 9/2014 | Leanna et al. | |
| 9,089,341 B2 * | 7/2015 | Chomas | A61B 18/1492 |
| 9,089,668 B2 * | 7/2015 | Chomas | A61B 17/12186 |
| 9,339,291 B2 * | 5/2016 | Aggerholm | B29C 59/021 |
| 9,770,319 B2 * | 9/2017 | Pinchuk | A61F 2/0108 |
| 2002/0013599 A1 | 1/2002 | Limon et al. | |
| 2002/0161388 A1 * | 10/2002 | Samuels | A61M 25/10 428/36.9 |

(56) References Cited

U.S. PATENT DOCUMENTS

| | | | |
|---|---|---|---|
| 2002/0183777 A1* | 12/2002 | Shannon | A61M 25/104 606/192 |
| 2003/0158571 A1 | 8/2003 | Esch et al. | |
| 2003/0158574 A1 | 8/2003 | Esch et al. | |
| 2003/0233115 A1 | 12/2003 | Eversull et al. | |
| 2005/0038468 A1* | 2/2005 | Panetta | A61M 25/104 606/200 |
| 2005/0085841 A1 | 4/2005 | Eversull et al. | |
| 2005/0085842 A1 | 4/2005 | Eversull et al. | |
| 2005/0101986 A1* | 5/2005 | Daniel | A61F 2/013 606/200 |
| 2005/0137696 A1* | 6/2005 | Salahieh | A61F 2/2439 623/2.11 |
| 2005/0165352 A1 | 7/2005 | Henry et al. | |
| 2005/0251194 A1* | 11/2005 | McHale | A61M 25/1038 606/192 |
| 2005/0256562 A1* | 11/2005 | Clerc | A61F 2/95 623/1.11 |
| 2005/0261662 A1* | 11/2005 | Palasis | A61M 25/0084 604/173 |
| 2005/0267516 A1 | 12/2005 | Soleimani et al. | |
| 2005/0288629 A1* | 12/2005 | Kunis | A61M 25/10 604/22 |
| 2006/0100662 A1* | 5/2006 | Daniel | A61B 17/221 606/200 |
| 2006/0173244 A1* | 8/2006 | Boulais | A61B 1/015 600/156 |
| 2006/0173475 A1* | 8/2006 | Lafontaine | A61B 17/32075 606/159 |
| 2006/0173490 A1* | 8/2006 | Lafontaine | A61F 2/013 606/200 |
| 2006/0190074 A1* | 8/2006 | Hill | A61F 2/2475 623/2.18 |
| 2006/0195118 A1* | 8/2006 | Richardson | A61B 17/221 606/113 |
| 2006/0253148 A1* | 11/2006 | Leone | A61B 17/12136 606/200 |
| 2006/0253186 A1 | 11/2006 | Bates | |
| 2007/0027534 A1 | 2/2007 | Bergheim et al. | |
| 2007/0208408 A1 | 9/2007 | Weber et al. | |
| 2007/0233224 A1 | 10/2007 | Leynov et al. | |
| 2008/0065145 A1* | 3/2008 | Carpenter | A61F 2/01 606/200 |
| 2008/0183132 A1* | 7/2008 | Davies | A61M 25/104 604/103.09 |
| 2008/0215008 A1 | 9/2008 | Nance et al. | |
| 2008/0243081 A1 | 10/2008 | Nance et al. | |
| 2008/0275485 A1* | 11/2008 | Bonnette | A61F 2/01 606/200 |
| 2008/0319526 A1 | 12/2008 | Hill et al. | |
| 2009/0082800 A1 | 3/2009 | Janardhan | |
| 2009/0163846 A1* | 6/2009 | Aklog | A61M 1/3616 604/6.11 |
| 2009/0182278 A1 | 7/2009 | Eversull et al. | |
| 2009/0287182 A1 | 11/2009 | Bishop et al. | |
| 2009/0287183 A1 | 11/2009 | Bishop et al. | |
| 2009/0287203 A1* | 11/2009 | Mazzone | A61M 25/1006 606/21 |
| 2010/0076482 A1 | 3/2010 | Shu et al. | |
| 2010/0094209 A1 | 4/2010 | Drasler et al. | |
| 2010/0094392 A1 | 4/2010 | Nguyen et al. | |
| 2010/0168785 A1 | 7/2010 | Parker | |
| 2010/0168836 A1 | 7/2010 | Kassab | |
| 2010/0179583 A1 | 7/2010 | Carpenter et al. | |
| 2010/0179584 A1* | 7/2010 | Carpenter | A61F 2/01 606/200 |
| 2010/0179585 A1* | 7/2010 | Carpenter | A61F 2/013 606/200 |
| 2010/0179647 A1* | 7/2010 | Carpenter | A61F 2/01 623/2.11 |
| 2010/0185231 A1 | 7/2010 | Lashinski | |
| 2010/0191276 A1 | 7/2010 | Lashinski | |
| 2010/0211095 A1* | 8/2010 | Carpenter | A61F 2/0105 606/200 |
| 2010/0217175 A1 | 8/2010 | Pah | |
| 2010/0234855 A1* | 9/2010 | Wahr | A61B 17/12136 606/127 |
| 2010/0312268 A1 | 12/2010 | Belson | |
| 2010/0324589 A1* | 12/2010 | Carpenter | A61M 25/0015 606/200 |
| 2011/0106135 A1* | 5/2011 | Thompson | A61F 2/0105 606/200 |
| 2011/0130657 A1* | 6/2011 | Chomas | A61F 2/013 604/246 |
| 2011/0144690 A1 | 6/2011 | Bishop et al. | |
| 2011/0152763 A1 | 6/2011 | Bishop et al. | |
| 2011/0251679 A1 | 10/2011 | Wiemeyer et al. | |
| 2011/0282379 A1 | 11/2011 | Lee et al. | |
| 2011/0295304 A1* | 12/2011 | Jonsson | A61B 17/12109 606/200 |
| 2012/0035646 A1 | 2/2012 | McCrystle | |
| 2012/0078343 A1 | 3/2012 | Fish | |
| 2012/0083877 A1 | 4/2012 | Nguyen et al. | |
| 2012/0109182 A1 | 5/2012 | Belson | |
| 2012/0172915 A1 | 7/2012 | Fifer et al. | |
| 2012/0172916 A1 | 7/2012 | Fifer et al. | |
| 2012/0172917 A1 | 7/2012 | Fifer et al. | |
| 2012/0172918 A1 | 7/2012 | Fifer et al. | |
| 2012/0172919 A1 | 7/2012 | Fifer et al. | |
| 2012/0172920 A1 | 7/2012 | Fifer et al. | |
| 2012/0179033 A1 | 7/2012 | Merhi | |
| 2012/0289996 A1* | 11/2012 | Lee | A61F 2/012 606/200 |
| 2013/0144328 A1* | 6/2013 | Weber | A61M 25/0074 606/200 |
| 2013/0253571 A1* | 9/2013 | Bates | A61F 2/2427 606/200 |
| 2013/0281788 A1 | 10/2013 | Garrison | |
| 2014/0067050 A1* | 3/2014 | Costello | A61F 2/2436 623/2.11 |
| 2014/0142598 A1* | 5/2014 | Fulton, III | A61B 17/320725 606/159 |
| 2014/0200648 A1 | 7/2014 | Newell et al. | |
| 2014/0277096 A1* | 9/2014 | Richter | A61F 2/013 606/200 |
| 2014/0277417 A1 | 9/2014 | Schraut et al. | |
| 2014/0277565 A1 | 9/2014 | Clerc | |
| 2014/0296959 A1 | 10/2014 | Leanna et al. | |
| 2015/0157455 A1 | 6/2015 | Hoang et al. | |
| 2015/0320552 A1 | 11/2015 | Letac et al. | |
| 2015/0320556 A1 | 11/2015 | Levi et al. | |
| 2015/0342718 A1 | 12/2015 | Weber et al. | |
| 2015/0343178 A1* | 12/2015 | Fulton, III | A61M 25/0074 604/509 |
| 2016/0136389 A1* | 5/2016 | Christian | A61M 25/003 604/523 |
| 2016/0317276 A1* | 11/2016 | Groh | A61F 2/013 |
| 2017/0281381 A1 | 10/2017 | Harris | |
| 2017/0333183 A1 | 11/2017 | Backus | |

FOREIGN PATENT DOCUMENTS

| | | | |
|---|---|---|---|
| WO | 03039345 A2 | 5/2003 | |
| WO | 2016126524 A1 | 8/2016 | |
| WO | 2016/176591 A1 | 11/2016 | |
| WO | 2017027289 A1 | 2/2017 | |
| WO | WO-2020180866 A1 * | 9/2020 | A61B 34/20 |
| WO | WO-2022047485 A1 * | 3/2022 | A61B 17/221 |

OTHER PUBLICATIONS

Hackworth et al., "Development and First Application of Bistable Expandable Sand Screen", SPE International Society of Petroleum Engineers, Oct. 2003.

* cited by examiner

MEDICAL DRAIN DEVICE

CROSS-REFERENCE TO RELATED APPLICATIONS

This application claims the benefit of priority under 35 U.S.C. § 119 to U.S. Provisional Application Ser. No. 62/462,692, filed Feb. 23, 2017, the entirety of which is incorporated herein by reference.

TECHNICAL FIELD

The invention relates generally to medical devices and more particularly to medical devices that are adapted for use in filtering and/or blocking of downstream flow within a body lumen and may allow for selective removal and/or draining of fluid and/or material from a body lumen.

BACKGROUND

A number of endovascular procedures are presently performed on patients with atherosclerotic disease and the like to treat stenotic or occluded regions within the patient's blood vessels, such as the peripheral, coronary, carotid, or cerebral arteries or veins. For example, an angioplasty procedure may be used to dilate a stenosis, or an atherectomy and/or thrombectomy may be performed to open occluded regions. A stent or other prosthesis may be implanted to retain patency of a vessel, either alone or in conjunction with these procedures. Furthermore, a therapeutic agent may be delivered to the treatment site within a blood vessel, as desired.

One of the problems with such procedures, however, is that embolic material may be released during the procedure, and travel downstream where it may become lodged creating an embolism, such as arterial or venous embolisms, or otherwise cause harm to the patient. For example, ischemic stroke may occur when such emboli are released and travel to the patient's brain. For another example, pulmonary embolism may occur when such emboli are released and travel to the patient's lungs.

A continuing need exists for improved vascular devices and methods for use in conjunction with vascular surgery. For example, there is a need for improved vascular devices that may be deployed to capture and remove embolic material from the body. There is also need for improved vascular devices that may be deployed to isolate therapeutic agents within a treatment area, and selectively allow for the removal of the therapeutic agents from the isolated treatment area, while reducing downstream and/or systematic dispersion of the therapeutic agents within the patient's body.

SUMMARY

The disclosure is directed to several alternative designs, materials and methods of manufacturing medical device structures and assemblies, and uses thereof.

A medical device is disclosed. The medical device comprises an elongate tubular member having a distal portion and a distal end, a proximal portion and a proximal end, and defining a tube lumen extending from the distal end to the proximal end. An expandable member is disposed on the distal portion of the elongate tubular member and extends distally beyond the distal end. The expandable member defines an expandable member lumen that is in fluid communication with the tube lumen. The expandable member is configured to expand from a collapsed delivery configuration to a distally-open expanded configuration. A valve member is in fluid communication with the tube lumen, the valve member configured to selectively block and selectively allow for flow through the tube lumen.

Alternatively or additionally to any of the embodiments above, the expandable member is biased to the distally-open expanded configuration.

Alternatively or additionally to any of the embodiments above, the medical device further includes an outer tubular member movable between an extended position in which the outer tubular member extends over the expandable member and maintains the expandable member in the collapsed delivery configuration, and a retracted position in which the outer tubular member is proximal of the expandable member, permitting the expandable member to expand into the distally-open expanded configuration.

Alternatively or additionally to any of the embodiments above, the expandable member includes a proximal end and a distal end, and wherein when the expandable member is in the expanded configuration, the distal end of the expandable member has an outer diameter that is greater than an outer dimeter of the proximal end of the expandable member.

Alternatively or additionally to any of the embodiments above, the expandable member includes a proximal end and a distal end, wherein the distal end of the expandable member defines a distal opening into the expandable member lumen, and the distal opening is smaller when the expandable member is in the collapsed delivery configuration than when in the expanded configuration.

Alternatively or additionally to any of the embodiments above, the expandable member includes a proximal end and a distal end, and wherein when the expandable member is in the distally-open expanded configuration, the expandable member tapers from a wider diameter portion near the distal end to a narrower diameter portion near the proximal end.

Alternatively or additionally to any of the embodiments above, the expandable member, when in the distally-open expanded configuration, is configured to funnel embolic material into the tube lumen.

Alternatively or additionally to any of the embodiments above, the expandable member is configured to at least partially allow fluid to flow there through while filtering embolic material from the fluid.

Alternatively or additionally to any of the embodiments above, the expandable member is configured to stop fluid flow there through when deployed.

Alternatively or additionally to any of the embodiments above, the expandable member includes a proximal end and a distal end, wherein the proximal end of the expandable member is attached to the distal end of the elongate tubular member.

A medical device comprising an elongate tubular member defining a tube lumen. An expandable member is disposed on a distal portion of the elongate tubular member, and extends distally beyond a distal end of the elongate tubular member. The expandable member is configured to expand from a collapsed delivery configuration to a distally-open expanded configuration, wherein when in the distally-open expanded configuration the expandable member defines a funnel configured to direct material into the tube lumen.

Alternatively or additionally to any of the embodiments above, further including a valve member disposed on a proximal portion of the elongate tubular member, the valve member configured to selectively block and selectively allow for flow through the tube lumen.

Alternatively or additionally to any of the embodiments above, further including an outer tubular member movable first position in which the outer tubular member extends over the expandable member and maintains the expandable member in the collapsed delivery configuration, and a second position in which the outer tubular member is removed from the expandable member, permitting the expandable member to expand into the expanded configuration.

Alternatively or additionally to any of the embodiments above, the expandable member is configured to at least partially allow flow of fluid there through while filtering embolic material.

Alternatively or additionally to any of the embodiments above, the expandable member is configured block fluid flow there through when deployed.

A method of treatment is disclosed. The method comprising introducing a medical device into a blood vessel of a patient, the medical device including: an elongate tubular member having a distal portion and a distal end, a proximal portion and a proximal end, and defining a tube lumen extending from the distal end to the proximal end; an expandable member disposed on the distal portion of the elongate tubular member and extending distally beyond the distal end, the expandable member defining an expandable member lumen that is in fluid communication with the tube lumen, the expandable member being configured to expand from a collapsed delivery configuration to a distally-open expanded configuration; and a valve member disposed on the proximal portion of the elongate tubular member, the valve member configured to selectively block and selectively allow for flow through the tube lumen. The method further including advancing the medical device, with the expandable member in the collapsed delivery configuration, through the vessel in a retrograde direction to a position downstream of a treatment site; and expanding the expandable member from the collapsed delivery configuration to the distally-open expanded configuration.

Alternatively or additionally to any of the embodiments above, the method further including, performing a procedure at the treatment site.

Alternatively or additionally to any of the embodiments above, wherein the procedure includes one or more of angioplasty, atherectopmy, thrombectomy, stent deployment, and therapeutic agent delivery.

Alternatively or additionally to any of the embodiments above, the method further including, opening the valve member to allow for flow from the blood vessel through the tube lumen.

Alternatively or additionally to any of the embodiments above, wherein expanding the expandable member includes establishing apposition of at least a portion of the expandable member with a wall of the blood vessel.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE FIGURES

FIG. 10 is a partial side view of the distal portion of the example medical device of FIG. 1 in an expanded configuration downstream of the treatment site, with another medical device being delivered there through.

Figure 1:
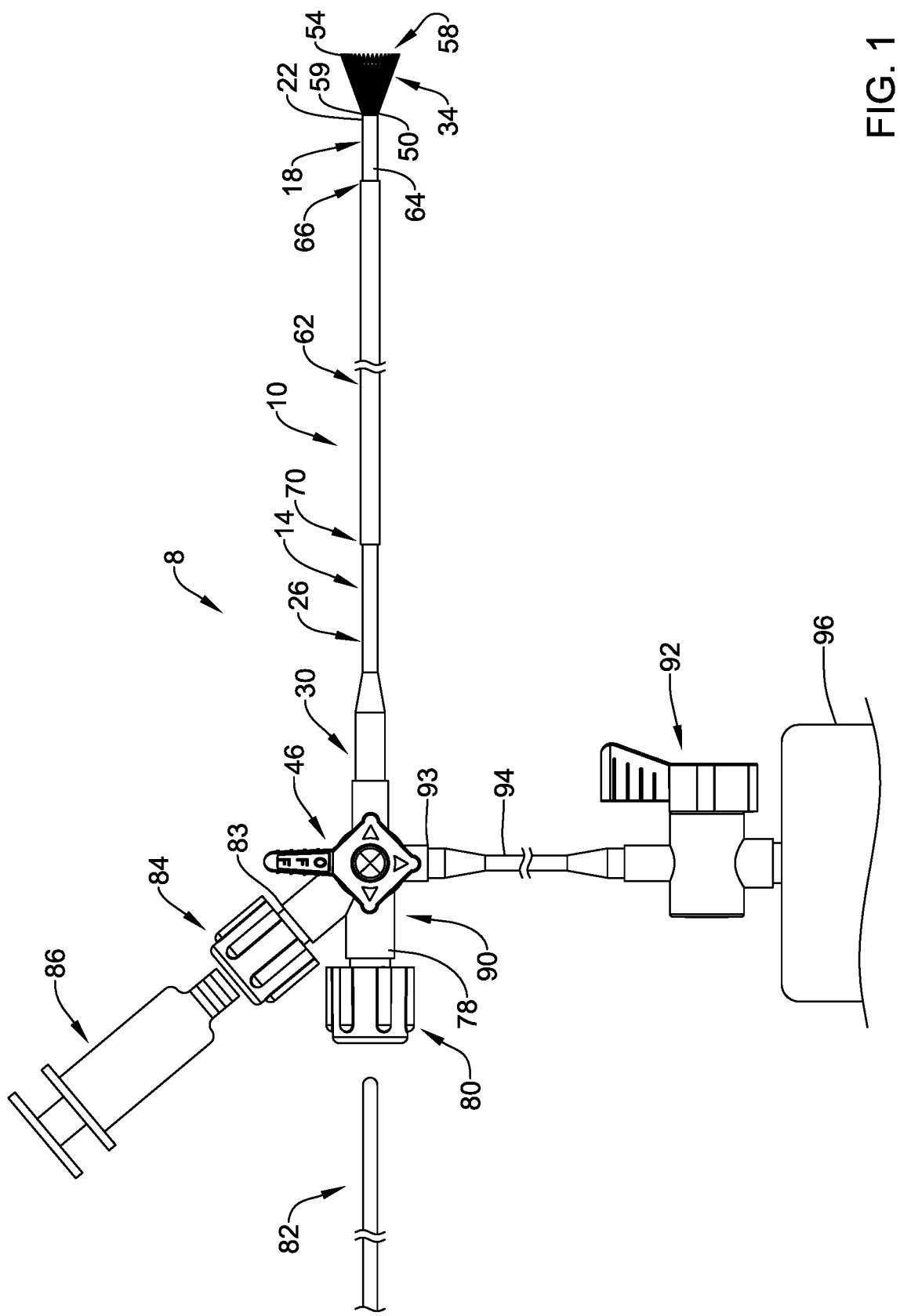
FIG. 1 is a partial side view of an example medical device system, including an example medical device having an elongate tubular member and an expandable member disposed on the distal portion of the elongate tubular member.

While the invention is amenable to various modifications and alternative forms, specifics thereof have been shown by way of example in the drawings and will be described in greater detail below. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

The terms "upstream" and "downstream" refer to a position or location relative to the direction of fluid flow, such as blood flow, through a particular element or location, such as a vessel (e.g. an artery or a vein), a treatment site, and the like.

The term "retrograde" when referring to the advancement of a device within a blood vessel means the device is being advanced in a direction that is against the normal direction of blood flow within the vessel.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout several views. The detailed description and drawings are intended to illustrate but not limit the claimed invention.

Some embodiments relate to a percutaneously-deployable medical device that may be employed downstream of a treatment site within a body lumen and may allow for selective removal and/or draining of fluid and/or material from a body lumen. For example, the medical device may be deployed when there is a concern with embolic material being released from the treatment site. For another example, the medical device may be deployed when there is a desire to isolate materials, such as therapeutic agents, within an isolated portion of the body lumen including the treatment site. The medical device may include an expandable portion that may establish apposition with a body lumen wall, and a lumen in fluid communication with the expandable portion that may allow for selective removal and/or draining of fluid and/or material from the body lumen while the device is deployed. The medical device may be introduced into the body lumen and advanced through a body lumen in a retrograde direction in a collapsed delivery configuration, with or without the aid of a separate delivery catheter or device. The expandable portion of the medical device may then be deployed to an expanded configuration downstream of the treatment site, and may establish apposition with the wall of the body lumen. Then, one or more of several functions or events may occur. For example, the medical device may be used as a downstream embolic protection filter and/or drain while a procedure is performed at the treatment site. In some embodiments, the expandable portion may include a filter that is permeable to fluid, thereby allowing for perfusion of blood and other fluids there through, while collecting embolic material, and selectively allowing for the draining of fluid and embolic material from the patient. In other embodiments, the filter may be impermeable to fluid, and act as a blocking member to isolate the area being treated, while selectively allowing for the draining of fluid and/or material from the patient.

Figure 2:
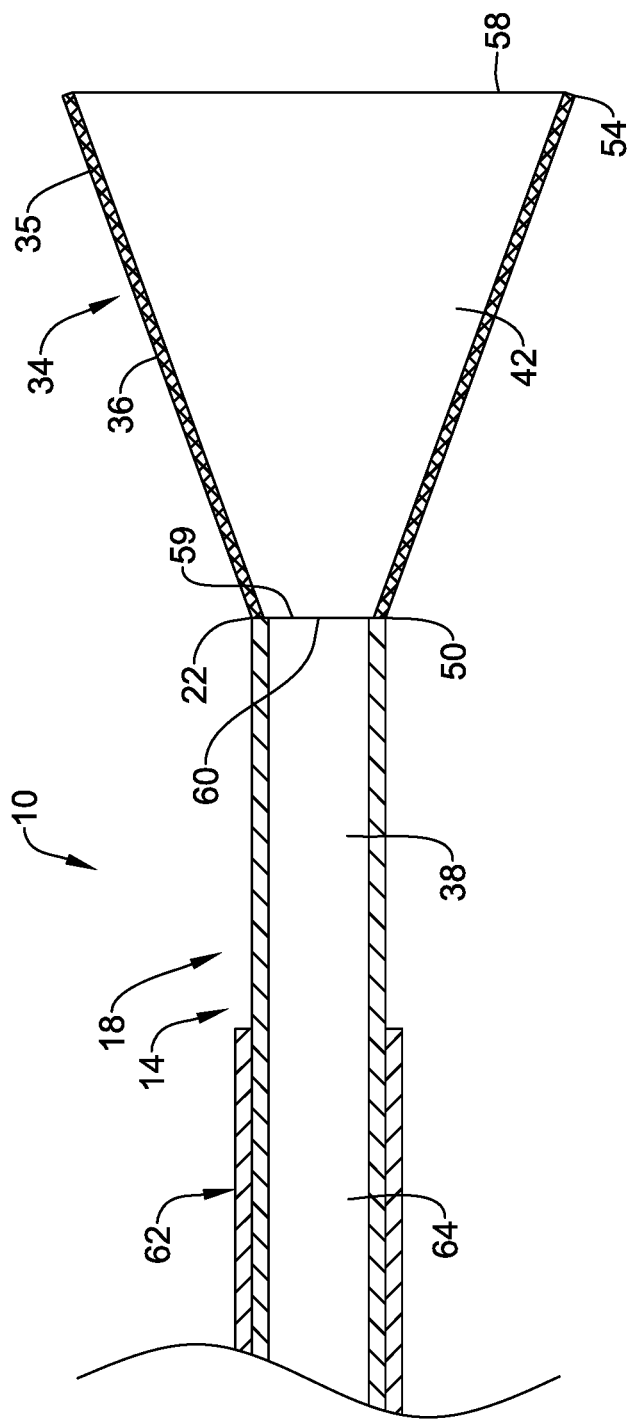
FIG. 2 is a partial cross sectional side view of a distal end of the example medical device of FIG. 1.

FIG. 1 schematically illustrates an example medical device system 8 including an example medical device 10, and FIG. 2 shows a cross section of a distal portion of the medical device 10. The medical device 10 may comprise an elongated tubular member 14 having a distal portion 18 and a distal end 22, a proximal portion 26 and a proximal end 30, and defining a tube lumen 38 extending from the distal end 22 to the proximal end 30. The distal portion 18 may have a size and shape for facilitating insertion within a body lumen, for example, a blood vessel. The medical device 10 may include an expandable member 34 disposed on the distal portion 18 of the elongate tubular member 14. The expandable member 34 defines an expandable member lumen 42 that is in fluid communication with the tube lumen 38. The expandable member 34 includes a distal end 54 and a proximal end 50. The distal end 54 of the expandable member 34 defines a distal mouth or opening 58 into the expandable member lumen 42. The proximal end 50 of the expandable member 34 defines a proximal opening 59, which is in fluid communication with both the expandable member lumen 42 and an opening 60 defined in the distal end 22 of the elongated tubular member 14. As such, fluid and/or material may flow through the distal opening 58 into the expandable member lumen 42 and through the proximal opening 59 into the tube lumen 38.

The proximal end 50 of the expandable member 34 is coupled to the distal portion 18 of the elongate tubular member 14. The expandable member 34 may extend distally beyond the distal end 22 of the elongate tubular member 14. The proximal end 50 of the expandable member 34 may be coupled to the outer surface of the distal portion 18. Alternatively, or additionally, the proximal end 50 of the expandable member 34 may be coupled to inner surface (e.g. in the lumen 38) of the distal portion 18. In yet further embodiments, the proximal end 50 of the expandable member 34 extends into the wall of the distal portion 18 of the tubular member 14, and is thereby attached thereto. In some cases the expandable member 34 is a separate component from the tubular member 14, and is attached to the tubular member 14 using a suitable attachment technique, such as adhesive bonding, welding, soldering, brazing, molding, bonding, extruding, heat shrinking, such as using a heat shrink tubing, or the like, or others. In some cases, the expandable member 34 is a part of and/or is a component of the tubular member 14, and as such, is an extension of the tubular member 14 that may be expandable relative to a remainder of the tubular member 14.

The expandable member 34 is configured to expand (e.g. selectively expand) from a collapsed delivery configuration to a distally-open expanded configuration. An example expandable member 34 is shown in a collapsed delivery configuration in FIG. 4, which will be discussed in more detail below. When in the collapsed delivery configuration, the expandable member 34, or at least a portion thereof, has a smaller dimension than when in the distally-open expanded configuration. In the collapsed delivery configuration, the expandable member 34 may be configured for delivery and advancement within a body lumen, such as a blood vessel. In some embodiments, the expandable member 34 in the collapsed delivery configuration may have an outer diameter along its length that may be generally equal to or less than an outer diameter of the elongate tubular member 14.

Figure 3:
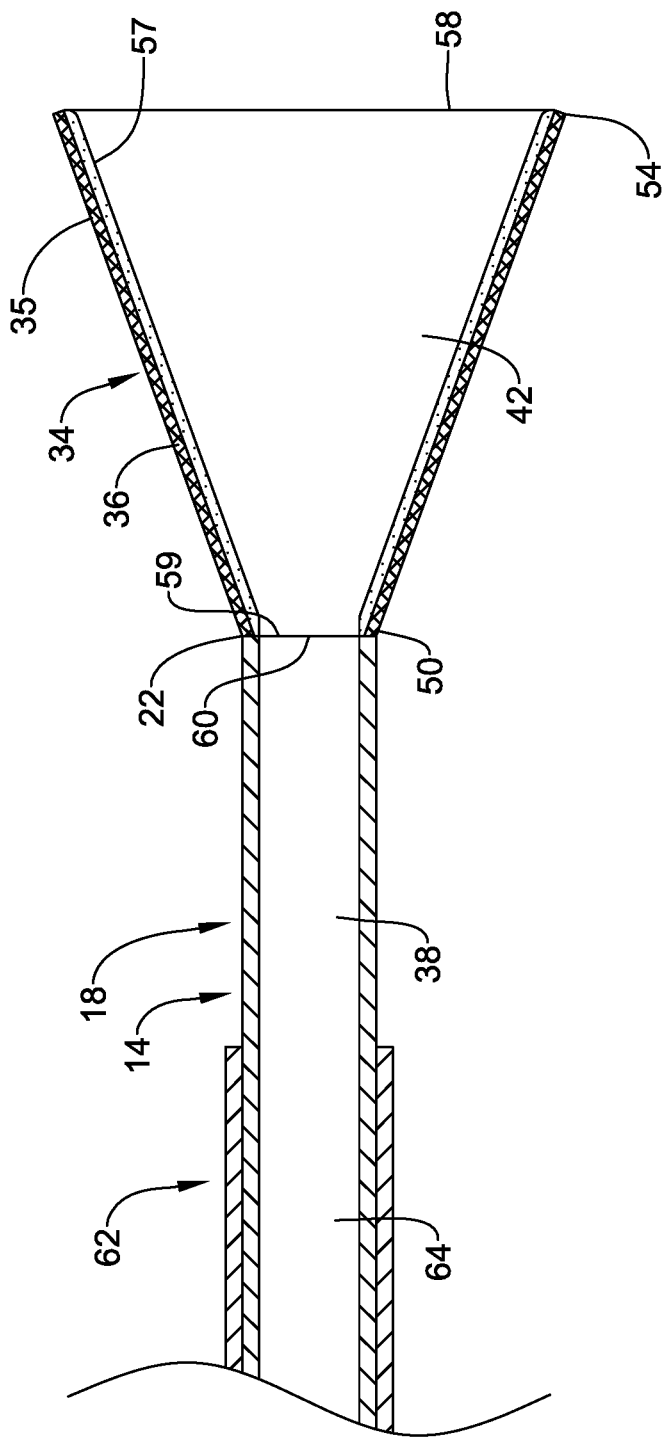
FIG. 3 is a partial cross sectional side view of a distal end of the example medical device of FIG. 1 including a membrane as part of the expandable member.

FIGS. 1-3 show the example expandable member 34 in the distally-open expanded configuration. When in the distally-open expanded configuration, the expandable member 34, or at least a portion thereof, has a larger dimension than when in the collapsed delivery configuration. When in the distally-open expanded configuration the expandable member 34 may be configured to establish apposition with the wall of the body lumen in which the device is used, such as the wall of a blood vessel. As such, when in the expanded configuration, at least a portion of the expandable member 34 may include a diameter that is the same as or larger than the lumen diameter of the body lumen in which the device is used, such as a blood vessel.

Additionally, the expandable member 34, when in the distally-open expanded configuration, may be configured to funnel or direct material, such as fluid, blood, and/or embolic material, from the body lumen into the tube lumen 38. In general, when in the expanded configuration, the expandable member 34 forms a distally-opening structure generally expanding radially from an outer diameter of the elongate tubular member 14. In some embodiments, the expandable member 34 achieves its greatest diameter and/or outer extent at the distal end 54 in the expanded configuration.

For example, when the expandable member 34 is in the distally-open expanded configuration, the expandable member 34 may taper from a larger diameter distal portion to a smaller diameter proximal portion. When in the expanded configuration, the expandable member 34 may have at least a part thereof that defines a shape which may be generally described as a truncated cone, including a first smaller diameter (inner and/or outer diameter) near the proximal end 50, and a second larger diameter (inner and/or outer diameter) near the distal end 54. For example, the diameter of the lumen 42 may taper from larger near the distal end 54 to smaller near the proximal end 50 and/or the outer diameter of the expandable member 34 may taper from larger near the distal end 54 to smaller near the proximal end 50. In some embodiments, the outer diameter near the proximal end 50 may be the same or similar to the outer diameter of the elongate tubular member 14. Also, in some cases, the diameter of the lumen 42 near the proximal end 50 may be the same or similar to the diameter of the tube lumen 38. As can be appreciated, when the expandable member 34 is in the expanded configuration, the distal mouth or opening 58 into the expandable member lumen 42 may be larger than the proximal opening 59.

As can also be appreciated, the distal end 54 and/or distal opening 58 may have a first outer diameter in the collapsed delivery configuration and a second outer diameter in the expanded configuration. The distal end 54 and/or distal opening 58 will generally be smaller in the collapsed delivery configuration than when in the expanded configuration.

In some embodiments, a medical device 10 may include an outer tubular member 62 disposed about the elongate tubular member 14. The outer tubular member 62 includes a distal end 66 and a proximal end 70, and defines a lumen 64 extending from the proximal to the distal end. In some embodiments, the proximal end 70 may include a finger grip or handle, or the like, to facilitate engagement and use by an operator. The distal portion of the outer tubular member 62 may have a size and shape for facilitating insertion within a body lumen, for example, a blood vessel. The lumen 64 may include a diameter that is generally equal to or greater than an outer diameter of the elongate tubular member 14. Additionally, the lumen 64 has a diameter for slidably receiving the expandable member 34 in its collapsed configuration there through. Alternatively, the lumen 64 may have an enlarged distal region (not shown) for receiving the expandable member 34 therein proximate the distal end of the lumen 64, and a narrow proximal region (also not shown) for receiving the elongate tubular member 14 there through.

Figure 4:
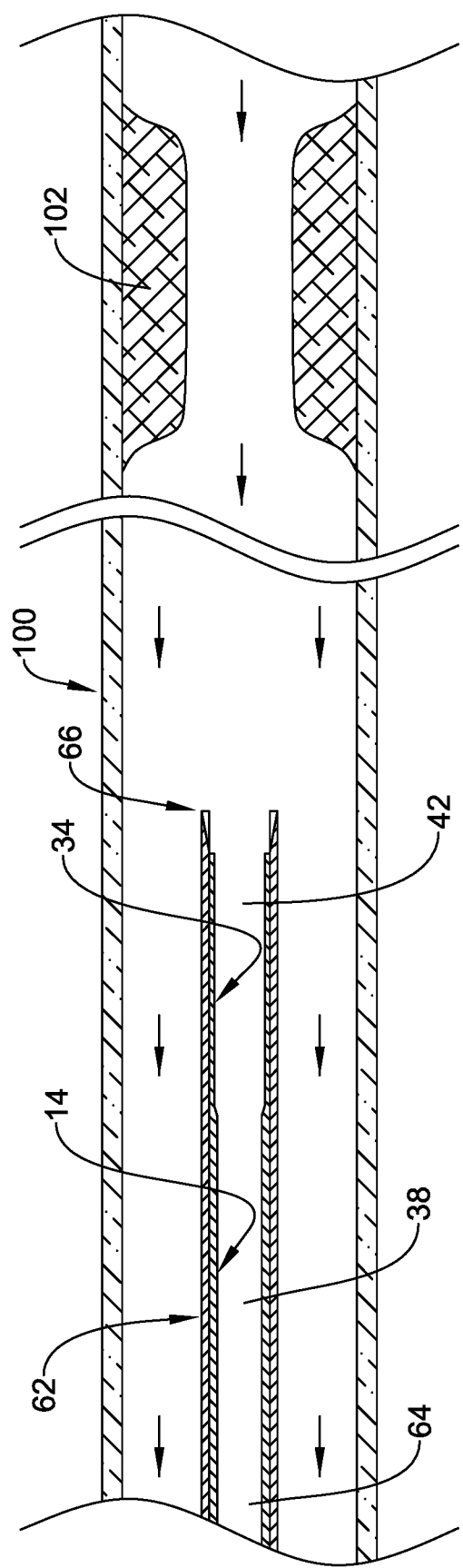
FIG. 4 a partial side view of the distal portion of the example medical device of FIG. 1 being delivered in a retrograde fashion to a location within a body lumen downstream of a treatment site with the expandable member in a collapsed delivery configuration.

As can be appreciated in FIGS. 4-6, which will be discussed in more detail below, the outer tubular member 62 may be configured to axially move and/or longitudinally translate relative to the elongate tubular member 14, between an extended position in which the outer tubular member 62 extends over the expandable member 34 and maintains the expandable member 34 in the collapsed delivery configuration, and a retracted position in which the outer tubular member 62 is proximal of the expandable member 34, permitting the expandable member 34 to expand into the expanded configuration. As shown in FIG. 4, in the collapsed delivery configuration, the expandable member 34 may have an outer diameter along its length that may be generally equal to or smaller than an inner diameter (lumen 64 diameter) of the distal portion of the outer tubular member 62. In some embodiments, the outer tubular member 62 may include or be used as a delivery sheath and/or a retrieval sheath for the expandable member 34. In some embodiments, the tubular member 62 may take the form of a catheter, sheath, hypotube, endoscope, or other tubular medical device suitable for the intended use.

The expandable member 34, or portions thereof, may be biased and/or self-biased and/or self-expanding into the distally open expanded configuration. For example, the expandable member 34, or portions thereof, when not constrained in the collapsed condition, will automatically expand to the distally open expanded configuration. In the relaxed and/or unconstrained state, the expandable member 34 may be biased to the distally open expanded configuration. The expandable member 34 may assume the collapsed delivery configuration when urged, for example, into the lumen 64 of the outer tubular member 62, but will automatically expand to the distally open expanded configuration when extended out of the lumen 64. In some cases, expandable member 34, or portions thereof, may include elastic and/or super-elastic material that may be deformed from the distally open expanded configuration, but that can elastically recover to the distally open expanded configuration when released.

However, other embodiments are contemplated where other mechanisms of expansion of the expandable member 34 are contemplated. For example, expandable member 34 may be balloon expandable from the collapsed configuration to the expanded configuration. In some contemplated embodiments, a separate balloon catheter could be inserted through the medical device 10, and inflated under the expandable member 34 to achieve expansion thereof. In some embodiments, an inflatable structure may be incorporated into the structure of the expandable member itself, and inflation of such a structure would achieve expansion of the expandable member. Furthermore, systems including one or more pull wires, tethers, and the like are also contemplated to achieve expansion of the expandable member. In some contemplated embodiments, the expandable member 34 may be made of, or include, a shape-memory material, such as a shape memory polymer or shape memory metal, and expansion could be achieved through the application of a temperature change or electrical current to the material. A wide variety of other devices and mechanisms generally known to provide for expansion of a medical device component are also contemplated for use in providing for expansion of the expandable member 34.

Referring to FIG. 2, the expandable member 34 may include and/or be made of an expandable frame 35. The frame 35 may comprise a plurality of struts, splines, rings, wires, filaments, mesh and/or a solid bolus and/or sheet of material. For example, in some embodiments, the expandable frame 35 may include an expandable tubular structure cut from a tubular monolith of material to form struts, akin to a self-expanding stent structure. In some embodiments, the expandable frame 35 may include one or more wires or filaments or hoops attached together to form an expandable structure. In some embodiments, the expandable frame may include an expandable mesh and/or an expandable sheet of material, or the like.

In some cases the expandable member 34 and/or the expandable frame 35 may include a plurality of apertures 36 defined there through. The plurality of apertures 36 may facilitate perfusion blood flow through the expandable member 34 while allowing the capturing and/or filtering of material larger than the apertures. For example, the expandable member 34 and/or the expandable frame 35 may be configured to filter embolic debris while permitting the perfusion of blood there through. In other embodiments, however, the expandable member 34 and/or the expandable frame 35 may not include any apertures, but rather, may form a solid occlusion member and/or blocking member and/or funnel member to effectively prevent the downstream flow of fluid, such as blood or therapeutic agents, when deployed.

Alternatively, or additionally, the frame 35 may act as a support structure for a permeable or non-permeable layer or membrane. For example, with reference to FIG. 3, the expandable member 34 may include a layer or membrane 57 of material attached to the frame 35. The membrane 57 may be a permeable membrane having a plurality of openings or pores there through. The plurality of openings or pores through the membrane 57 may facilitate perfusion blood flow through the membrane 57 while capturing and/or filtering material larger than the openings or pores. For example, membrane may have a pore size in the range of about 0.05-0.30 mm, which may be used to capture embolic material that is large enough to cause substantial risk of harm to the patient, yet still allow for adequate perfusion. However, the size of the openings or pores can vary as desired, depending upon the desired function of the expandable member. The membrane 57 may be a polymeric sheet, such as polyethylene, with holes or pores provided therein, for example, by drilling, or a thin metal sheet with holes or pores provided therein, for example, by laser drilling. In other embodiments, the membrane 57 may not be permeable, and may not include any openings or pores there through, and as such, may form a solid occlusion member and/or blocking member and/or funnel member to effectively prevent the downstream flow of fluid when the expandable member 34 is deployed. The membrane 57 may be connected to the frame as desired, with some examples including adhesively bonding, tethering, sewing, soldering, welding, brazing, and the like.

While not expressly illustrated, the expandable member 34 may further include a soft, flexible, and/or stretchable/expandable ring disposed on and/or about the exterior surface on or near the distal end 54 thereof. The ring may provide a sealing member and/or cushion against the wall of the vessel to reduce irritation or abrasion of the inner surface of the vessel wall as well as prevent the leakage of blood and/or embolic material around the expandable member 34.

Referring back to FIG. 1, the medical device 10 further includes a valve member 46, such as a stop cock, in fluid communication with the tube lumen 38. The valve member 46 is configured to selectively block and selectively allow for flow through the tube lumen 38. In the embodiment shown, the valve member 46 is disposed on the proximal portion 26 of the elongate tubular member 14. In other embodiments, the valve member may be disposed at other locations, for example further downstream in the system, or more distally on the tubular member 14. In this particular embodiment, the valve member 46 is part of a hub assembly 90 attached to the proximal end 30 of the elongate tubular member 14. The hub assembly 90 may also include a drain port 93 in selective fluid communication with the tube lumen 38 through the valve member 46. A drain tube 94 may be part of the system, and may be connected to the drain port 93, leading to a collection and/or storage device 96, such as a bag, bottle, or the like. When the valve member 46 is open, it may allow for fluid and/or material to flow through the medical device 10 and ultimately into the storage device 96 of the system 8. For example, fluid and/or material may selectively flow through the expandable member lumen 42, through the tube lumen 38, through the hub assembly 90 including the valve member 46, through the drain port 93, through the drain tube 94 and into the storage device 96.

The example embodiment shown also includes an additional valve member 92 disposed between the drain tube 94 and the storage device 96. This additional valve member 92 may be configured to selectively block and selectively allow for flow from the drain tube 94 into the storage device 96. This may be closed to allow the storage device 96 to be removed and/or changed and/or emptied, while reducing the risk of fluid leaking. Additionally, in some embodiments, because the valve member 92 is in fluid communication with the tube lumen 38, it may also be used to selectively block and/or selectively allow for flow through the tube lumen 38, as desired.

The hub assembly 90 may include other structures and/or devices that allow for access to the tube lumen 38. For example, the hub assembly 90 may include a port 78 that may be designed to facilitate introduction of a device 82 into the tube lumen 38. The port 78 may include a seal member 80, such as a Tuohy Borst adapter, to help manage fluid backflow while still allowing device access to the lumen 38. The device 82 may include any device suitable for use in the particular procedure being performed, and may be included in the system 8. Some example devices may include a guidewire; a catheter, such as a guide catheter, a balloon catheter, a stent delivery catheter, a therapeutic agent delivery catheter, or the like; an atherectomy device; a thrombectomy device; or the like, or any other devices that may be desired and configured for insertion through the lumen 38. Such devices may be used in providing a treatment to the patient, for example, at the treatment site upstream of the deployed expandable member 34. Alternatively, such devices may be used to loosen and/or unclog material that may get stuck within the lumen 38.

Alternatively, or in addition, the hub assembly 90 may include a port 83 that may be designed to facilitate introduction of and/or aspiration of a fluid or material to or from the lumen 38. The port 83 may include a fitting 84, such as a luer fitting and/or adapter, or the like, configured to mate with a fluid delivery or aspiration source, and to help manage fluid leakage, while still allowing fluid access to the lumen 38. A fluid delivery and/or aspiration device 86, such as a syringe, or the like, may also be included with the system 8. Such a device 86 may be used, for example, to provide aspiration and/or suction to the lumen 38 to help loosen and/or unclog material that may get stuck within the lumen 38. Further, such a device 86 may be used, for example, to provide and/or deliver a fluid or material to the body lumen, such as therapeutic agents, marker material, saline, or the like.

Figure 5:
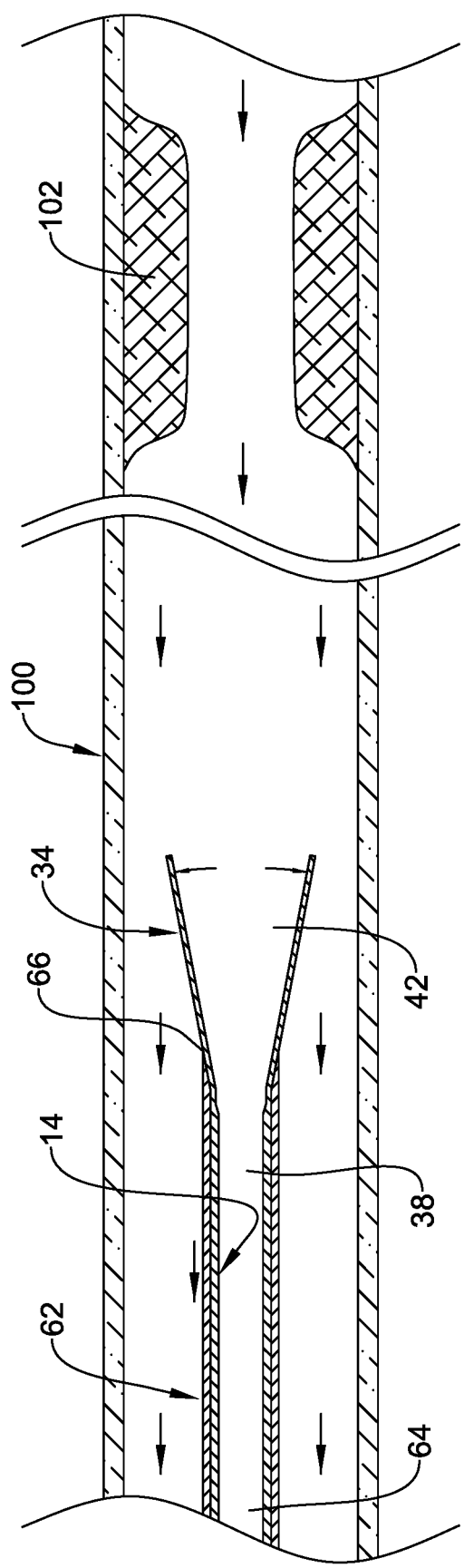
FIG. 5 is a partial side view of the example medical device of FIG. 4, with the expandable member being partially expanded downstream of the treatment site.
Figure 6:
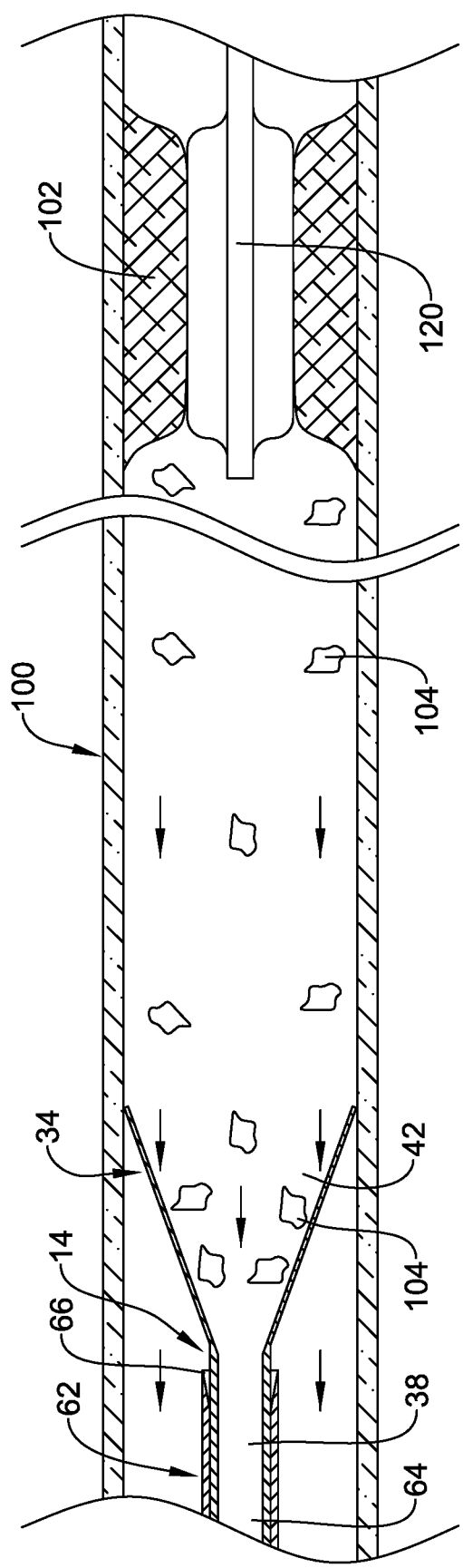
FIG. 6 is a partial side view of the example medical device of FIG. 4, in an expanded configuration downstream of the treatment site.

Referring now to FIGS. 4-6, one example of use of the example medical device 10 will be described. As seen in FIG. 4, the medical device 10 may be introduced into a body lumen of a patient, such as a blood vessel 100 of a patient, and advanced in a collapsed delivery configuration in a retrograde direction in the body lumen to a position downstream of a treatment site 102. In this particular example, the expandable member 34 is self-expanding, and the outer tubular member 62 is used as a delivery sheath and/or a retrieval sheath for the expandable member 34. In FIG. 4, the outer tubular member 62 is in an extended position in which the outer tubular member 62 extends over the expandable member 34 and maintains the expandable member 34 in the collapsed delivery configuration. The medical device 10 may be introduced and advanced with or without the aid of a separate delivery catheter or device, such as a separate introducer sheath (not shown), a guide catheter (not shown), a guidewire (not shown), or the like. Once the medical device 10 is positioned as desired downstream of the treatment site 102, the expandable member 34 may then be deployed.

In FIG. 5, the expandable member 34 has been partially deployed by moving the outer tubular member 62, or deployment sheath, in a proximal direction relative to the expandable member 34 and/or elongate tubular member 14. Because the expandable member 34 is self-expanding in this example, once unconstrained, the expandable member 34 will automatically begin to expand from a collapsed delivery configuration to a distally-open expanded configuration. As can be seen, a distal end region of the expandable member 34 begins to expand as the distal end region of the expandable member 34 is no longer constrained by the outer tubular member 62, and is shown partially deployed.

FIG. 6 shows the outer tubular member 62 moved to a fully retracted position, where the tubular member 62 is proximal of the expandable member 34, permitting the expandable member 34 to expand into the expanded configuration. When expanded, the expandable member 34 may establish apposition with a wall of the blood vessel 100. As such, in the distally open expanded configuration, the expandable member 34 may include a maximum diameter that substantially conforms to an inner surface of the vessel 100 at a position downstream of the treatment site 102. One or more procedures may then be performed at the treatment site 102, while the deployed medical device 10 may function as a downstream filter and/or funnel and/or drain.

Figure 7:
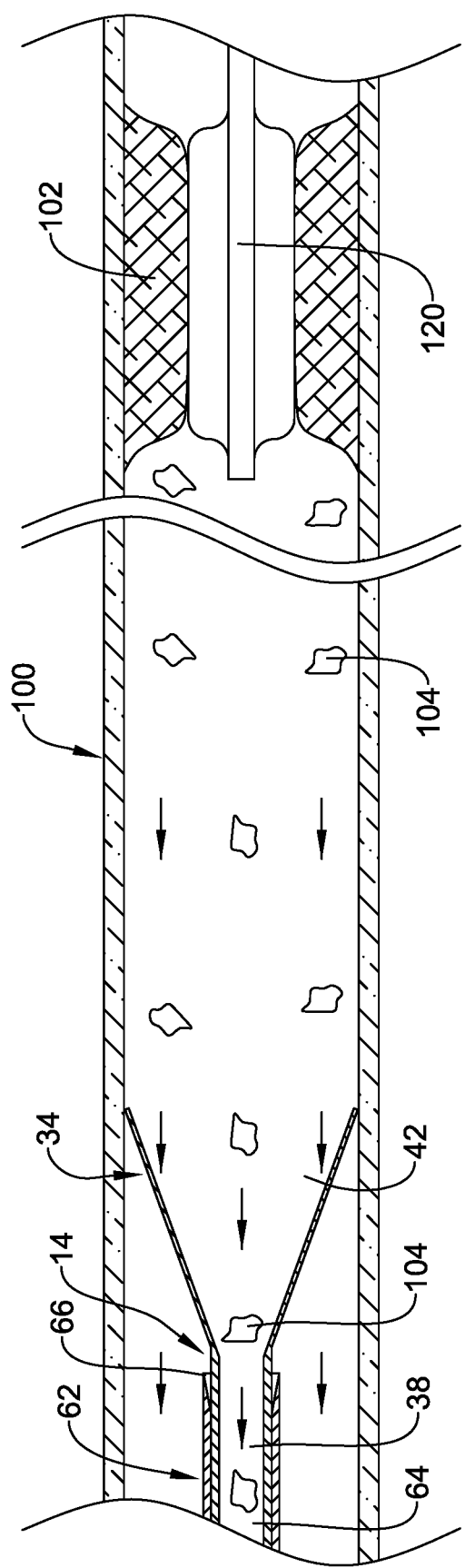
FIG. 7 is a partial side view of the example medical device of FIG. 4, in an expanded configuration downstream of the treatment site, with the valve member open and draining fluid through the lumen.

For example, an angioplasty procedure, an atherectomy and/or thrombectomy procedure, a stent or other prosthesis deployment procedure, a therapeutic agent delivery procedure, of the like, or others may be performed at the treatment site 102. In FIG. 6, a balloon catheter 120 is shown, for example, for performing an angioplasty procedure. During these procedures, embolic material 104 may break off or otherwise be released from the treatment site 102, travel downstream and enter the expandable member 34 through the distal opening 58. In this example, the expandable member 34 and/or the expandable frame 35 may be configured to filter embolic debris 104 while permitting the perfusion of blood there through. As such, the expandable member 34 and/or the expandable frame 35 may thus may prevent embolic material 104 from traveling further downstream where it may damage the patient. Additionally, the expandable member 34 and/or the expandable frame 35 may also direct and/or funnel the embolic material 104 and/or blood into the lumen 38. As shown in FIG. 7, a user may selectively drain fluid and/or embolic material from the patient through the lumen 38 of the medical device 10, for example, by selectively opening the valve member 46 and/or the valve member 92. In this embodiment, the fluid and/or embolic material would selectively drain into the storage device 96.

After the procedure is complete and/or the desired amount of fluid and/or embolic material have been removed and/or drained from the patient, the device can be collapsed and removed from the patient. For example, the outer tubular member 62 may be advanced distally relative to the tubular member 14 and into contact with the expandable member 34, and then advanced further distally to progressively collapse the expandable member 34 from the expanded configuration to the collapsed delivery configuration for withdrawal from the vasculature.

Figure 8:
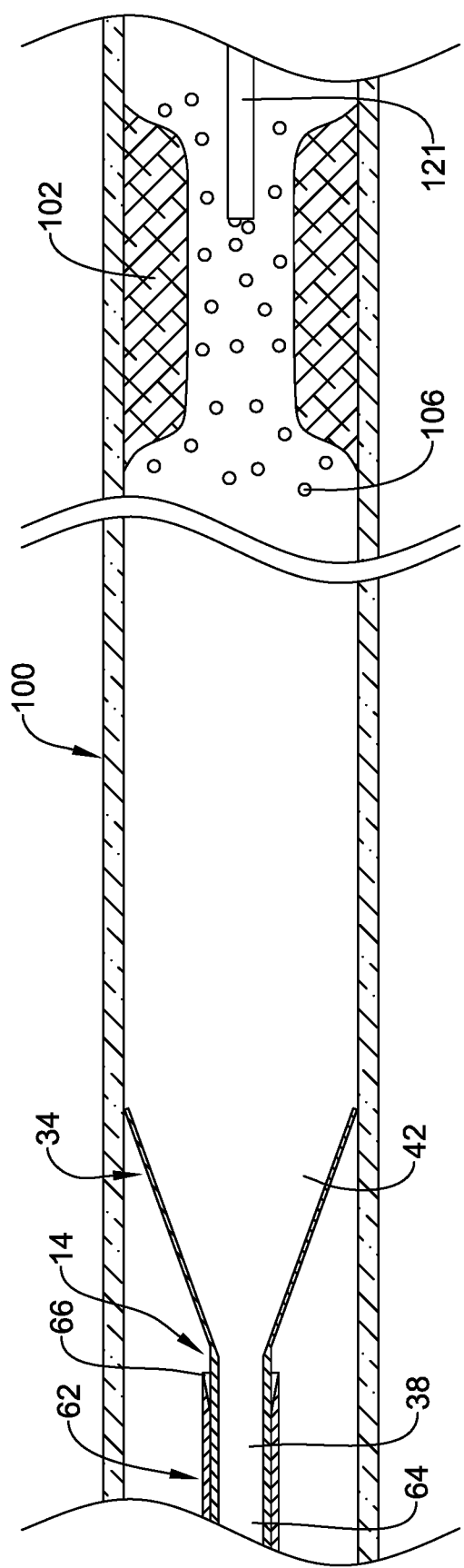
FIG. 8 is a partial side view of the distal portion of an example medical device in an expanded configuration downstream of the treatment site.
Figure 9:
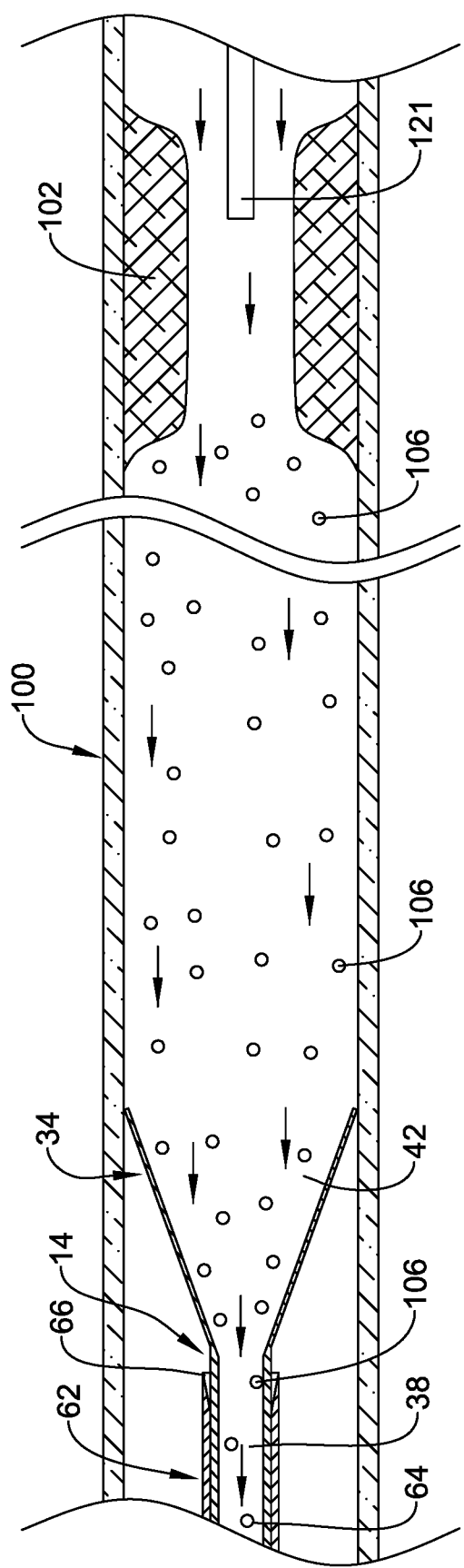
FIG. 9 is a partial side view of the example medical device of FIG. 8, in an expanded configuration downstream of the treatment site, with the valve member open and draining fluid through the lumen.

As can be appreciated, in other embodiments, the expandable member 34 and/or the expandable frame 35 may not be permeable and/or not include any apertures, but rather, may form a solid occlusion member and/or blocking member and/or funnel member to effectively prevent perfusion or the downstream flow of fluid or material such as blood, embolic material, or therapeutic agents, when deployed. FIGS. 8 and 9 can be used to describe one example such embodiment.

In FIG. 8, the expandable member 34 has been delivered as discussed above, and has established apposition with the wall of the blood vessel 100. In this embodiment, however, the expandable member 34 and/or expandable frame 35 does not include any apertures, but rather, forms a solid occlusion member and/or blocking member and/or funnel member to effectively prevent perfusion or the downstream flow of fluid or material such as blood, embolic material, or therapeutic agents, when deployed. As shown in FIG. 8, a drug delivery catheter 121, or the like, may deliver a therapeutic agent 106 to the treatment site 102. The expandable member 34 may substantially reduce and/or prevent the downstream flow and/or perfusion of fluid. As such, the therapeutic agent may be isolated to the area in and around the treatment site 102. When desired, for example after a desired dwell time, the therapeutic agent 106 and fluid around the treatment site may be removed and/or drained from the patient thought the medical device 10. As shown in FIG. 9, a user may selectively drain the therapeutic agent 106 and/or fluid and/or embolic material from the patient through the lumen 38 of the medical device 10, for example, by selectively opening the valve member 46 and/or the valve member 92. The fluid and/or embolic material, including the therapeutic agent 106 would selectively drain into the storage device 96. This is one example of using the medical device 10 to maintain an increased concentration of drug or other therapeutic agents within an isolated region of a vessel. This is also an example of using the medical device 10 to selectively allow for the removal or draining of the therapeutic agents from the isolated treatment area, while reducing downstream and/or systematic dispersion of the therapeutic agents within the patient's body.

After the procedure is complete and/or the desired amount of fluid and/or embolic material have been removed and/or drained from the patient, the device can be collapsed and removed from the patient. For example, the outer tubular member 62 may be advanced distally relative to the tubular member 14 and into contact with the expandable member 34, and then advanced further distally to progressively collapse the expandable member 34 from the expanded configuration to the collapsed delivery configuration for withdrawal from the vasculature.

Figure 10:
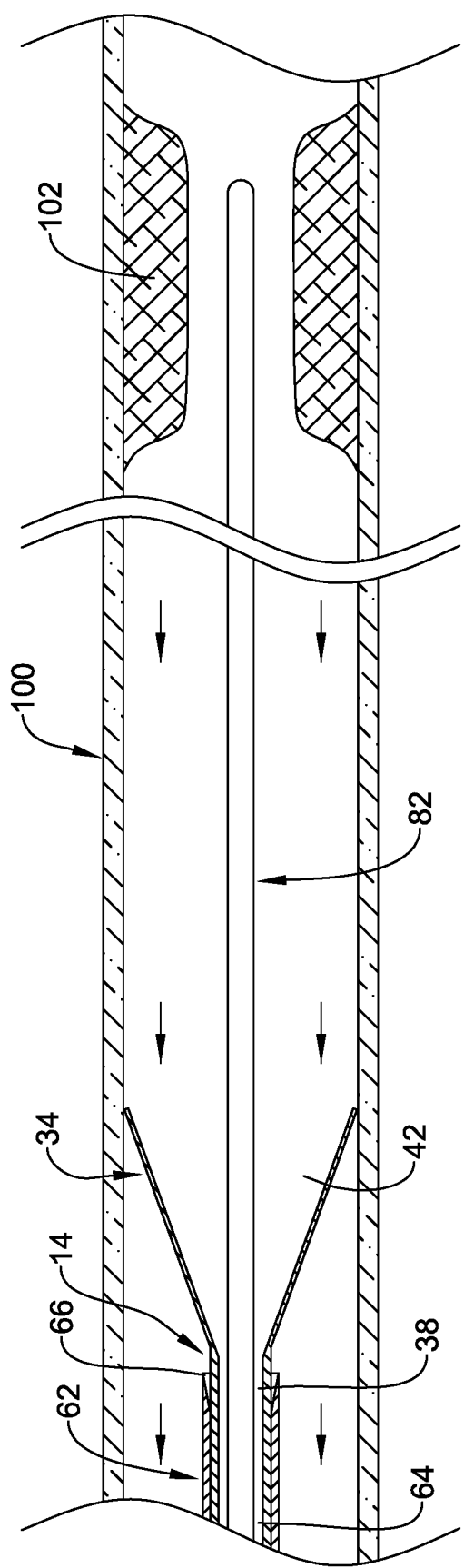

As may also be appreciated, the medical device 10 may also be used to deliver other devices there through. FIG. 10 shows one example of this. In FIG. 10, the expandable member 34 has been delivered as discussed above, and has established apposition with a wall of the blood vessel 100. The expandable member 34 and/or expandable frame 35 may be permeable or non-permeable, as discussed above, depending on if perfusion is desired or not. In this case, perfusion is shown. Another medical device 82 may be introduced through the device 10. For example, the device 82 may be introduced into the lumen 38, for example through port 78, as discussed above with reference to FIG. 1. The device 82 may be advanced thought the lumen 38, and into the blood vessel 100 of the patient in a retrograde direction in the body lumen to the treatment site 102. The device 82 may include any device suitable for use in the particular procedure being performed, and may be included in the system 8. Some example devices may include a guidewire; a catheter, such as a guide catheter, a balloon catheter, a stent delivery catheter, a therapeutic agent delivery catheter, or the like; an atherectomy device; a thrombectomy device; or the like, or any other devices that may be desired and configured for insertion through the lumen 38. Such devices may be used in providing a treatment to the patient, for example, at the treatment site upstream of the deployed expandable member 34. Alternatively, such devices may be used to loosen and/or unclog material that may get stuck within the lumen 38. One or more procedures may then be performed at the treatment site 102, while the deployed medical device 10 may function as a downstream filter and/or funnel and/or drain.

After the procedure is complete, the medical device 82 may be removed from the patient. Additionally, after the procedure is complete and/or the desired amount of fluid and/or embolic material have been removed and/or drained from the patient, the device 10 can be collapsed and removed from the patient. For example, the outer tubular member 62 may be advanced distally relative to the tubular member 14 and into contact with the expandable member 34, and then advanced further distally to progressively collapse the expandable member 34 from the expanded configuration to the collapsed delivery configuration for withdrawal from the vasculature.

In any of the above examples or procedures, it may be desirable to apply suction and/or aspiration and/or infusion through the device 10. For example, if the lumen gets clogged and/or if it is desired to increase the rate of flow out through the lumen 38, suction and/or aspiration and/or a flush may be applied to the lumen 38, through the use of fluid delivery and/or aspiration device 86, as discussed above with reference to FIG. 1. Additionally, it is also contemplated that fluid, such as saline or other therapeutic agents, or the like, may be delivered to the blood vessel 100 through the device 10. For example, fluid or a therapeutic agent may be delivered through the lumen 38 and into the patient through the use of fluid delivery and/or aspiration device 86, as discussed above with reference to FIG. 1.

It is also contemplated that more than one such medical device 10 may be used and/or deployed with in a patient at a time and/or during a procedure. For example, in cases where a blood vessel may include one or more branches downstream of a treatment site, it may be desirable to deploy multiple medical device 10, for example in each of the branches.

The elongate tubular member 14 and/or the outer tubular member 62 and/or the hub assembly 90, and/or the expandable member 34 (including the frame 35 and/or membrane 57), or other components of the device 10 or system 8 may be made from materials such as metals, a thin-film metal, metal alloys, polymers, metal-polymer composites, combinations thereof, or other suitable materials, and the like. Some examples of some suitable materials may include metallic materials and/or alloys such as stainless steel (e.g. 304v stainless steel or 316L stainless steel), nickel-titanium alloy (e.g., nitinol, such as super elastic or linear elastic nitinol), nickel-chromium alloy, nickel-chromium-iron alloy, cobalt alloy, nickel, titanium, platinum, or alternatively, a polymer material, such as a high performance polymer, or other suitable materials, and the like. Examples of suitable polymers may include polyurethane, a polyetherester such as ARNITEL® available from DSM Engineering Plastics, a polyester such as HYTREL® available from DuPont, a linear low density polyethylene such as REXELL®, a polyamide such as DURETHAN® available from Bayer or CRISTAMID® available from Elf Atochem, an elastomeric polyamide, a block polyamide/ether, a polyether block amide such as PEBA available under the trade name PEBAX®, silicones, polyethylene, Marlex high-density polyethylene, polyetheretherketone (PEEK), polyimide (PI), and polyetherimide (PEI), a liquid crystal polymer (LCP) alone or blended with other materials. Examples of suitable metallic materials may include stainless steels (e.g. 304v stainless steel), nickel-titanium alloys (e.g., nitinol, such as super elastic or linear elastic nitinol), nickel-chromium alloys, nickel-chromium-iron alloys, cobalt alloys, nickel, titanium, platinum, or other suitable materials, and the like.

In some embodiments, portions of the medical device 10 may be made of, may be doped with, may include a layer of, or otherwise may include a radiopaque material. Radiopaque materials are understood to be materials capable of producing a relatively bright image on a fluoroscopy screen or another imaging technique such as X-ray during a medical procedure. This relatively bright image aids the user of the device 10 in determining its location. Suitable materials can include, but are not limited to, bismuth subcarbonate, iodine, gold, platinum, palladium, tantalum, tungsten or tungsten alloy, and the like.

In some embodiments, portions of the medical device 10 may include one or more coatings disposed thereon, such as an anti-thrombus coating, a hydrophilic coating, a hydrophobic coating, or other coatings suitable for the procedure being performed.

It should be understood that although the above discussion was focused on a medical device and methods of use within the vascular system of a patient, other embodiments of medical devices or methods in accordance with the invention can be adapted and configured for use in other parts of the anatomy of a patient. For example, devices and methods in accordance with the invention can be adapted for use in the digestive or gastrointestinal tract, such as in the mouth, throat, small and large intestine, colon, rectum, and the like. For another example, devices and methods can be adapted and configured for use within the respiratory tract, such as in the mouth, nose, throat, bronchial passages, nasal passages, lungs, and the like. Similarly, the medical devices described herein with respect to percutaneous deployment may be used in other types of surgical procedures as appropriate. For example, in some embodiments, the medical devices may be deployed in a non-percutaneous procedure, including an open heart procedure. Devices and methods in accordance with the invention can also be adapted and configured for other uses within the anatomy.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

We claim:

1. A medical device comprising:
an elongate tubular member having a distal portion and a distal end, a proximal portion and a proximal end, and defining a tube lumen extending from the distal end to the proximal end;
an expandable member disposed on the distal portion of the elongate tubular member and extending distally beyond the distal end, the expandable member defining an expandable member lumen that is in fluid communication with the tube lumen, the expandable member being configured to expand from a collapsed delivery configuration to a distally-open expanded configuration, wherein the expandable member is configured to stop fluid flow there through when in the distally-open expanded configuration;
a first valve member disposed on the proximal portion of the elongate tubular member, the first valve member disposed in-line with the elongate tubular member and in fluid communication with the tube lumen, the first valve member configured to selectively block and selectively allow for flow through the tube lumen, wherein the first valve member is opened and closed by rotating an actuation member;
a collection device in fluid communication with the elongate tubular member; and
a second valve member disposed between the collection device and the elongate tubular member, wherein the second valve member is configured to selectively block and allow fluid flow through the elongate tubular member.

2. The medical device of claim 1, wherein the expandable member is self-expanding and is biased to the distally-open expanded configuration.

3. The medical device of claim 1, further including an outer tubular member movable between an extended position in which the outer tubular member extends over the expandable member and maintains the expandable member in the collapsed delivery configuration, and a retracted position in which the outer tubular member is proximal of the expandable member, permitting the expandable member to expand into the distally-open expanded configuration.

4. The medical device of claim 1, wherein the expandable member includes a proximal end and a distal end, and wherein when the expandable member is in the expanded configuration, the distal end of the expandable member has an outer diameter that is greater than an outer dimeter of the proximal end of the expandable member.

5. The medical device of claim 1, wherein the expandable member includes a proximal end and a distal end, wherein the distal end of the expandable member defines a distal opening into the expandable member lumen, and the distal opening is smaller when the expandable member is in the collapsed delivery configuration than when in the expanded configuration.

6. The medical device of claim 1, wherein the expandable member includes a proximal end and a distal end, and wherein when the expandable member is in the distally-open expanded configuration, the expandable member tapers from a wider diameter portion near the distal end of the expandable member to a narrower diameter portion near the proximal end of the expandable member.

7. The medical device of claim 1, wherein the expandable member, when in the distally-open expanded configuration, is configured to funnel embolic material into the tube lumen.

8. The medical device of claim 1, wherein the expandable member includes a proximal end and a distal end, wherein the proximal end of the expandable member is attached to the distal end of the elongate tubular member.

9. The medical device of claim 1, wherein the expandable member includes a frame fixed to the distal portion of the elongate tubular member, and a non-permeable membrane extending over the frame.

10. The medical device of claim 1, wherein the expandable member includes a flexible ring disposed on an exterior surface at a distal end of the expandable member.

11. A medical device comprising:
an elongate tubular member defining a tube lumen;
a self-expandable member disposed on a distal portion of the elongate tubular member, and extending distally beyond a distal end of the elongate tubular member, the expandable member being configured to expand from a collapsed delivery configuration to a distally-open expanded configuration, wherein when in the distally-open expanded configuration the expandable member defines a funnel configured to direct material into the tube lumen, wherein the expandable member is configured to block fluid flow there through when in the distally-open expanded configuration; and
a first valve member disposed on a proximal portion of the elongate tubular member, the first valve member disposed in-line with the elongate tubular member and configured to selectively block and selectively allow for flow through the tube lumen, wherein the first valve member is opened and closed by rotating an actuation member;
a collection device in fluid communication with the elongate tubular member; and
a second valve member disposed between the collection device and the elongate tubular member, wherein the second valve member is configured to selectively block and allow fluid flow through the elongate tubular member.

12. The medical device of claim 11, further including an outer tubular member movable first position in which the outer tubular member extends over the expandable member and maintains the expandable member in the collapsed delivery configuration, and a second position in which the outer tubular member is removed from the expandable member, permitting the expandable member to expand into the expanded configuration.

13. A method of treatment, the method comprising:
introducing a medical device into a blood vessel of a patient, the medical device including:
an elongate tubular member having a distal portion and a distal end, a proximal portion and a proximal end, and defining a tube lumen extending from the distal end to the proximal end;
an expandable member disposed on the distal portion of the elongate tubular member and extending distally beyond the distal end, the expandable member defining an expandable member lumen that is in fluid communication with the tube lumen, the expandable member being configured to expand from a collapsed delivery configuration to a distally-open expanded configuration, wherein the expandable member is configured to stop fluid flow there through when in the distally-open expanded configuration;
a first valve member disposed on the proximal portion of the elongate tubular member, the first valve member disposed in-line with the elongate tubular member and configured to selectively block and selectively allow for flow through the tube lumen, wherein the first valve member is opened and closed by rotating an actuation member;
a collection device in fluid communication with the elongate tubular member; and
a second valve member disposed between the collection device and the elongate tubular member;
advancing the medical device, with the expandable member in the collapsed delivery configuration, through the vessel in a retrograde direction to a position downstream of a treatment site;
expanding the expandable member from the collapsed delivery configuration to the distally-open expanded configuration; and
rotating the actuation member to selectively open and close the first valve member.

14. The method of claim 13, further including, performing a procedure at the treatment site.

15. The method of claim 14, wherein the procedure includes one or more of angioplasty, atherectomy, thrombectomy, stent deployment, and therapeutic agent delivery.

16. The method of claim 13, further including, opening the first valve member to allow for flow from the blood vessel through the tube lumen.

17. The method of claim 13, wherein expanding the expandable member includes establishing apposition of at least a portion of the expandable member with a wall of the blood vessel.

\* \* \* \* \*